United States Patent [19]

Allison et al.

[11] Patent Number: 5,748,491

[45] Date of Patent: May 5, 1998

[54] DECONVOLUTION METHOD FOR THE ANALYSIS OF DATA RESULTING FROM ANALYTICAL SEPARATION PROCESSES

[75] Inventors: Daniel B. Allison, Menlo Park, Calif.; James O. Bowlby, Jr., San Jose, Calif.

[73] Assignee: The Perkin-Elmer Corporation, Foster City, Calif.

[21] Appl. No.: 579,204

[22] Filed: Dec. 20, 1995

[51] Int. Cl.⁶ .......................... G06F 17/14; G06F 17/11
[52] U.S. Cl. .......................... 364/497; 364/572; 364/576
[58] Field of Search .......................... 364/497, 553, 364/570, 572, 576, 724.04, 735

[56] References Cited

U.S. PATENT DOCUMENTS

| | | |
|---|---|---|
| 4,532,548 | 7/1985 | Zwirn .......................... 358/166 |
| 4,675,095 | 6/1987 | Kambara et al. |
| 4,720,786 | 1/1988 | Hara . |

(List continued on next page.)

FOREIGN PATENT DOCUMENTS

WO 94/14131  6/1994  WIPO .

OTHER PUBLICATIONS

Zhao et al., "Investigation of block filtering and deconvolution for the improvement of lateral resolution and flaw sizing accuracy in ultrasonic testing," *Ultrasonics* 33:3, pgs. 187–194, May 1, 1995.

(List continued on next page.)

*Primary Examiner*—Emanuel T. Voeltz
*Assistant Examiner*—M. Kemper
*Attorney, Agent, or Firm*—Paul D. Grossman

[57] ABSTRACT

An improved signal processing method in a signal processor for performing the deconvolution of a signal resulting from an analytical separation process is disclosed. In a first aspect, a signal representing a plurality of partially separated sample zones is measured, a point-spread-function of the signal is determined, and the Fourier transform of the signal and the point-spread-function is taken. Next, a noise component n of the signal is determined and the value of a result signal A(f) is calculated using the following filter $$A(f) = \frac{(D(f)P^*(f))}{P^*(f)P(f) + n},$$

where D(f) is the Fourier transform of the signal, P(f) is the Fourier transform of the point-spread-function, and P*(f) is the complex conjugate of P(i). Finally, the inverse Fourier transform of the result A(f) is taken and reported as A(t). Preferably, the point-spread function is a Gaussian function having a standard deviation σ, where σ is determined using either an αβ tracker or the function $\sigma=(a+bt^2)^{1/2}$, where a and b are constants. In a second aspect of the invention, a plurality of possible point-spread-functions of the signal are determined and the above-described method is applied using each PSF. The value of the largest point-spread-function which provides a nonnegative result is determined, and the associated value of A(t) is reported. In a third aspect of the invention, a program storage device readable by a machine, tangibly embodying a program of instructions executable by a machine to perform the method steps of the first or the second aspects of the invention is provided.

9 Claims, 8 Drawing Sheets

SIGNAL PROCESSING SYSTEM

Report A(t)

U.S. PATENT DOCUMENTS

| | | |
|---|---|---|
| 4,811,218 | 3/1989 | Hunkapiller et al. . |
| 4,832,815 | 5/1989 | Kambara et al. . |
| 4,868,749 | 9/1989 | Kimura et al. . |
| 4,879,012 | 11/1989 | Kambara et al. . |
| 4,885,696 | 12/1989 | Hara . |
| 4,941,092 | 7/1990 | Hara et al. . |
| 4,958,281 | 9/1990 | Hara . |
| 5,091,652 | 2/1992 | Mathies et al. . |
| 5,273,632 | 12/1993 | Stockham et al. . |
| 5,274,240 | 12/1993 | Mathies et al. . |

OTHER PUBLICATIONS

Bilgen et al., "Restoration of Noisy Images Blurred by a Random Medium," Fifth Annual IEEE Symposium on Computer–Based Medical Systems Session 4A: Image Motion and Noise Reduction, pp. 250–256, Jun. 14–17, 1992.

Bilgen et al., "Restoration of Noisy Images Blurred by a Random Point Spread Function," 1990 International Symposium on Circuits and Systems, vol. 1, New Orleans, Louisiana, pp. 759–762, May 1–3, 1990.

Dore et al., "Experimental Determinaton of CT Point Spread Function," IEEE Engineering in Medicine & Biology Society 11th Annual International Conference, vol. 2, Seattle, Washington, pp.620–621, Nov. 12, 1989.

Javidi et al., "Image Deconvolultion by nonlinear signal processing," *Applied Optics* 28:15, pp. 3106–3111, Aug. 1, 1989.

Kondo et al., "Adaptive Image Restoration Using Constrained Deconvolution," The Transactions of the Institute of Electronics of Japan, Information and Comm. Engineers, E72:11, pp. 1243–1250, Nov. 1989.

1

DECONVOLUTION METHOD FOR THE ANALYSIS OF DATA RESULTING FROM ANALYTICAL SEPARATION PROCESSES

BACKGROUND

This invention relates to the analysis of data resulting from an analytical separation process using an improved deconvolution method.

The ability to separate and detect closely related chemical species is critically important in modern chemical and biochemical science. This is particularly true in the life sciences which involve the study of molecules that exist as complex mixtures of closely related species.

Analytical separation process separate individual components of a multicomponent mixture into individual sample zones based on the different migration rate of each component. Examples of such separation process include liquid chromatography, gas chromatography, electrophoresis, centrifugation, staged extraction, adsorption, and the like. An application of such processes of particular importance to modern biotechnology is DNA sequencing, which relies on the electrophoretic separation of polynucleotide fragments up to 1000 nucleotides in length which differ in size by only a single nucleotide.

Data resulting from analytical separation process is typically in the form of sample quantity as a function of time and/or position. For example, in the case of HPLC or real-time electrophoresis detectors, the data is in the form of concentration as a function of time. Alternatively, for autoradiographic electrophoresis detectors, the data is in the form of sample quantity as a function of position.

A problem which arises in the interpretation of such data is the identification of individual sample zones from among a plurality of zones which have not been completely resolved, i.e., overlapping sample zones. See FIG. 1. Lack of resolution is caused by the finite width of a sample zone due to the dispersive effects of diffusion, interfacial mass transfer, thermal profiles, sample injection, and other like effects. This problem is particularly acute when automatic data analysis is utilized, e.g., automatic base calling of DNA sequences, where hundreds of overlapping zones must be accurately resolved.

One particularly powerful class of methods useful for identifying individual sample zones in data containing overlapping sample zones is deconvolution. In deconvolution, a measured signal is considered to be a convolution of two separate signal functions—a "true" signal function representing the location of a hypothetical zone having zero width, and a point-spread-function (PSF) representing the non-zero width of each sample zone. In practice, the deconvolution process generally is implemented by taking the Fourier transform (FT) of the signal and a PSF, dividing the transformed signal by the transformed PSF, and performing an inverse Fourier transform of the result. In addition, a filtering operation may applied prior to taking the inverse Fourier transform to reduce the effect of noise on the deconvolved data.

Present deconvolution methods applied to data resulting from analytical separations use a "blind" deconvolution method with homomorphic filtering, e.g., U.S. Pat. No. 5,273,632, incorporated herein by reference in its entirety. Blind deconvolution methods utilize a constant PSF which is chosen without any reference to a particular application. This provides the advantage that the PSF need not be precisely know ahead of time. However, blind deconvolution methods suffer from a number of important limitations.

Because the PSF function is not optimized with respect to the signal, a highly discriminatory filter can not be effectively employed because application of such a filter to a non-optimized PSF would create high frequency noise. Furthermore, the transformed signal must be preconditioned prior to filtering to normalize the signal. This extra step can introduce unwanted noise into the final result. Finally, present methods do not account for the fact that the PSF can vary during the course of an analysis, thus making the fit between a constant PSF and the actual data necessarily suboptimal.

SUMMARY

The present invention is directed toward our discovery of an improved signal processing method in a signal processor for performing the deconvolution of a signal resulting from an analytical separation process, e.g., electrophoresis, HPLC or other like processes. The method of the invention uses a priori knowledge of the nature of the signal and/or adaptive parameter estimation techniques to tune a PSF used to estimate the width of a sample zone. The method has particular application in the area of automated DNA sequencing.

An object of our invention is to provide an improved signal processing method for identifying individual sample zones in a signal containing multiple overlapping sample zones wherein a highly discriminatory filter can be applied to the transformed signal, e.g., a Weiner filter.

Another object of our invention is to provide an improved signal processing method for identifying individual sample zones in a signal containing multiple overlapping sample zones wherein a PSF is determined using an application-specific model of the PSF which takes into account the variation of the PSF as a function of time and/or position in the signal.

Yet another object of our invention is to provide an improved signal processing method for identifying individual sample zones in a signal containing multiple overlapping sample zones wherein the value of the PSF is determined using adaptive parameter estimation techniques.

Another object of our invention is to provide an improved signal processing method which facilitates the automatic base-calling of DNA sequences.

In a first aspect, the foregoing and other objects of the invention are achieved by an improved signal processing method in a signal processor comprising the following steps. A signal D(t) representing a plurality of partially separated sample zones is measured in a data window and received by the processor. A point-spread-function of the signal is then determined for that data window, P(t), and the Fourier transform of the signal and the point-spread-function is taken. Next, a noise component n of the signal is determined and the value of a result signal A(f) is calculated, where $$A(f) = \frac{(D(f)P^*(f))}{P^*(f)P(f) + n}$$

where D(f) is the Fourier transform of the signal, P(f) is the Fourier transform of the point-spread-function, P*(f) is the complex conjugate of P(f), and n is the noise component of the signal. Finally, the inverse Fourier transform of the result signal A(f) is taken and reported as result signal A(t) in the time domain. This process is repeated for successive data windows until all of the signal has been processed.

In a first preferred embodiment, the point-spread function is a Gaussian function having a standard deviation σ, where σ is determined using an αβ tracker including constant terms α and β, where α is between 0.2 and 0.8 and $$\beta = \frac{\alpha^2}{(2-\alpha)}.$$

In a second preferred embodiment, the point-spread function is a Gaussian function having a standard deviation σ, where σ is determined using the function $$\sigma = (a+bt^2)^{1/2}$$

where a and b are constants.

In a second aspect of the invention, a plurality of possible point-spread-functions of the signal are determined. Then, the Fourier transform of each of the point-spread-functions is taken along with the Fourier transform of the signal. Next, an estimate of a noise component of the signal is determined and the value of a result signal A(f) is calculated for each point-spread-function, where $$A(f) = \frac{(D(f)P^*(f))}{P^*(f)P(f) + n}$$

where the variables D(f), P(f), P*(f), and n are as defined above. The inverse Fourier transform of the result signal A(f) is taken for each value of the point-spread function. Then, the value of the largest point-spread-function which provides a non-negative result signal in the data window is determined, and the associated value of A(t) is reported.

In a third aspect of the invention, a program storage device readable by a machine, tangibly embodying a program of instructions executable by a machine to perform the method steps of the first or the second aspects of the invention is provided.

In a forth aspect of the invention, a signal processor adapted to carry out the method steps of the first or the second aspects of the invention is provided.

These and other objects, features, and advantages of the present invention will become better understood with reference to the following description, drawings, and appended claims.

DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

The present invention is directed towards an improved signal processing method in a signal processor useful for identifying individual sample zones, or "peaks", present in a signal comprising a plurality of overlapping sample zones, such signal being generated by a detector monitoring an analytical separation process, e.g., chromatography, electrophoresis, centrifugation, staged extraction, adsorption, and the like. More specifically, the invention is directed toward an improved signal processing method in a signal processor for deconvolving such a signal. The invention is particularly well adapted for detecting individual electrophoretic sample zones in a signal containing multiple overlapping sample zones resulting from an automated DNA sequencing process.

Figure 1:
FIG. 1 is a schematic representation of overlapping sample zones in a signal.
Figure 2:
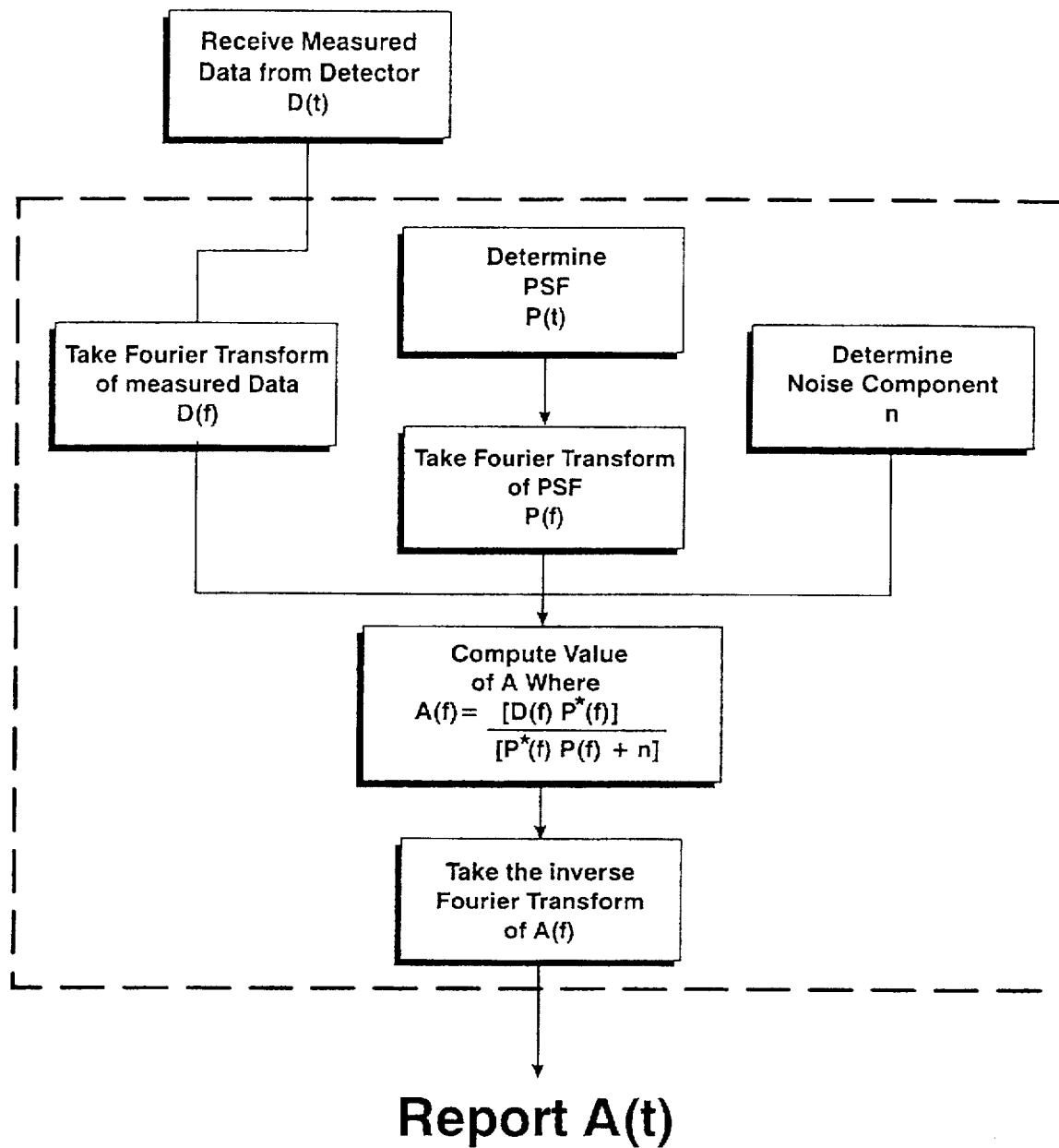
FIG. 2 is a flow chart of generally describing the signal processor of the present invention.

Generally, the method of the present invention is carried out as follows: (i) the Fourier transform of a signal in a data window is computed; (ii) a point-spread function of the signal is determined; (iii) the Fourier transform of the point-spread function is taken; (iv) a noise component of the signal is determined; (v) the value of a deconvolved result signal A(f) is determined by the formula $$A(f) = \frac{(D(f)P^*(f))}{P^*(f)P(f) + n}$$

where D(f) is the Fourier transform of the signal, P(f) is the Fourier transform of the point-spread-function, P*(f) is the complex conjugate of P(f), and n is a noise component of the signal; (vi) the inverse Fourier transform of the result signal A(f) is taken; (vii) the result signal in the time domain A(t) for the window is reported; and (viii) the window is indexed. Steps i–viii are repeated until all of the signal has been processed. FIG. 2 shows a representation of the signal processing system of the present invention.

The Signal:

The signal processor of the invention receives a signal generated by a detector which monitors the results of an analytical separation process, e.g., an electrophoretic separation. Such detectors may be "real-time" detectors which monitor the output of a separation during the separation, e.g., a HPLC chromatograph or a real-time electrophoresis scanner. Preferably the signal is generated by an electrophoresis scanner useful for separating and detecting the products of a DNA sequencing reaction, e.g., by Sanger-type sequencing, e.g., U.S. Pat. Nos. 4,811,218, 4,879,012, 4,832, 815, 4,675,095, and 5,274,240, each of which is incorporated by reference herein in its entirety. Alternatively, the detector may be a "snap-shot" detector which analyzes the results of a separation after the separation is completed, e.g., an autoradiographic or fluorescent scanner, e.g., U.S. Pat. No. 5,091,652, which is incorporated by reference herein in its entirety.

Such detectors may rely on any detectable signal which can be associated with a sample component. Exemplary detectors include detectors based on changes in fluorescence, absorbance, index of refraction, radioactivity, or the like. Preferably, the signal-to-noise ratio (S/N) of the signal is greater than 10 dB. More preferably, the sampling frequency of the signal is chosen to satisfy the Nyquist sampling theorem, i.e., the sampling frequency is at least twice the frequency of the highest frequency in the signal. Preferably, the signals are converted to digital form prior to processing using standard A/D conversion apparatus.

Figure 3:
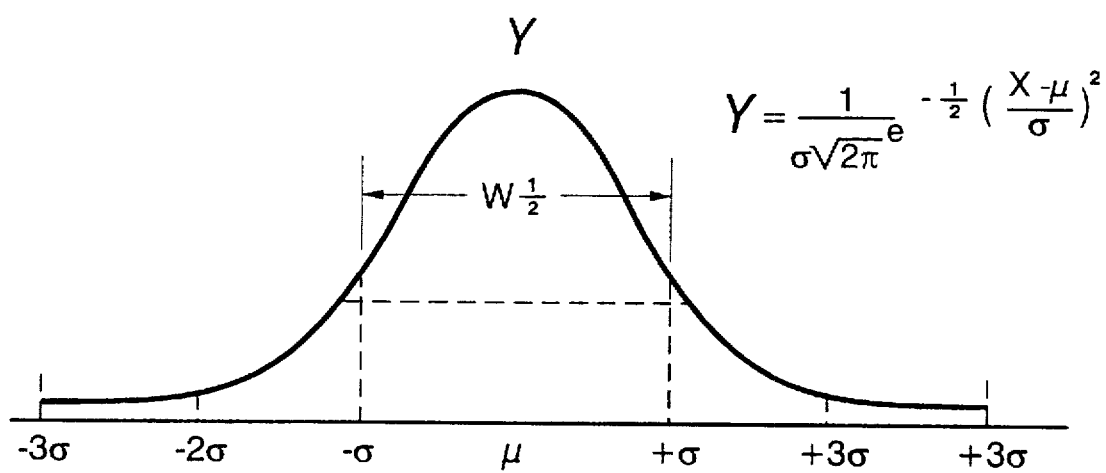
FIG. 3 depicts a normal or Gaussian distribution.

The Point-Spread-Function:

The term "point-spread function" or "PSF" as used herein refers to any model which approximates the signal or portions thereof. The model can be in the form of a function, or as a set of discrete values. Exemplary PSFs include functions such as cos, sin, $\cos^2$, Lorentzean, second order parabolic, Gaussian, or any other like function or combination of functions. Preferably, the PSF is a Gaussian function or a group of multiple Gaussian functions. A Gaussian function is characterized by a standard deviation a which is directly related to the width of the bell-shaped Gaussian curve, i.e., $w_{1/2}=2.35\sigma$ where $w_{1/2}$ is the full-width of a peak at half maximum height. See FIG. 3.

The ability of a deconvolution method to identify overlapping sample zones is directly related to how well the PSF approximates the signal, or how well "tuned" the PSF is to a particular signal. If the PSF is not properly tuned, the deconvolution process will not faithfully recover the "true" signal, and may result in the creation of spurious peaks and/or the loss of actual peaks. Given a Gaussian PSF, the parameter s is used to tune the PSF to the signal.

One method of choosing a σ which fits the signal is to assume that s is constant throughout the signal, e.g., Stockham et al., *Proceedings of the IEEE*, 63(4): 678–692 (1975). However, if the width of the sample zones change throughout the signal, the PSF will never be properly tuned to all of the measured signal. In fact, this is the situation in signal derived from a DNA sequencing operation, where the width of the sample zones in the spatial dimension decreases with increasing base number.

In one important aspect of the signal processor of the present invention, the value of a at a particular location in a signal derived from a DNA sequencing electrophoresis experiment is computed using an empirical function which describes the change in s as a function of time or location. By using a function to describe how a changes with base number rather than a using a constant value for σ, the PSF is better tuned to the signal throughout the data. One preferred expression which is used to describe the change in σ as a function of run time is, $$\sigma = (a+bt^2)^{1/2}$$

where a and b are constants which are chosen by fitting experimental data. Values of a and b are dependent on the conditions used for the electrophoretic separation, e.g., electrical field strength, gel concentration, buffer composition, temperature, and other like parameters which affect electrophoretic separations. In the case of automated DNA sequencing, under conditions typically used in the ABI Model 373 DNA Sequencer (Applied Biosystems Division, The Perkin-Elmer Corporation, Foster City, Calif. (ABI)), a is preferably about 8.61 $s^2$ and b is preferably about $5.53*10^{-7}$.

In another important aspect of the signal processor of the present invention, the value of a is determined using adaptive parameter estimation, where, as used herein, the terms "adaptive parameter estimation" or "adaptive tuning" refer to a process whereby the value of a parameter is determined with reference to previous values of that parameter in the same signal. Adaptive tuning has the advantage that the tuning algorithm can dynamically adapt to a signal in which the value of σ changes in an unpredictable manner.

Figure 5A:
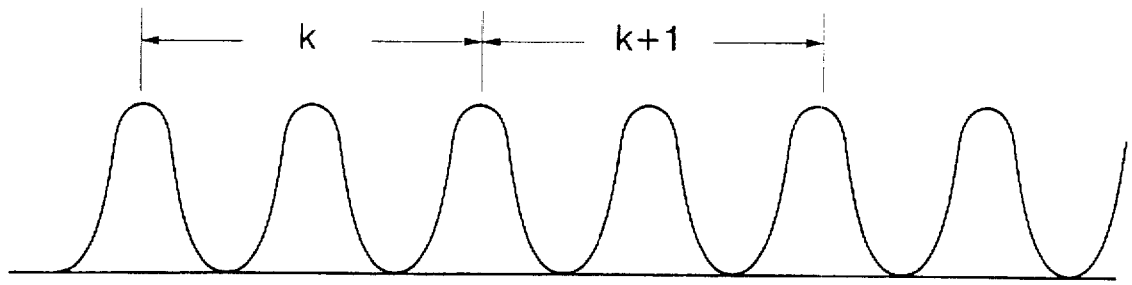
FIGS. 5A, 5B, and 5C show alternative methods for indexing a data window utilized in the signal processor of the invention.
Figure 5B:
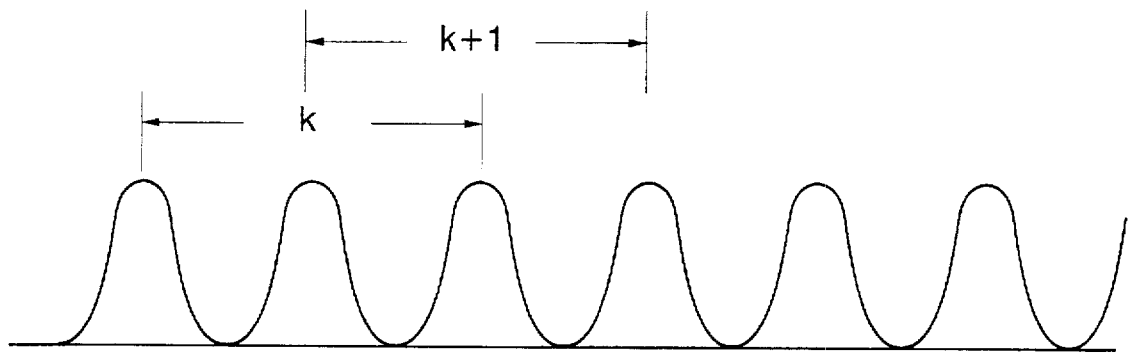
Figure 5C:
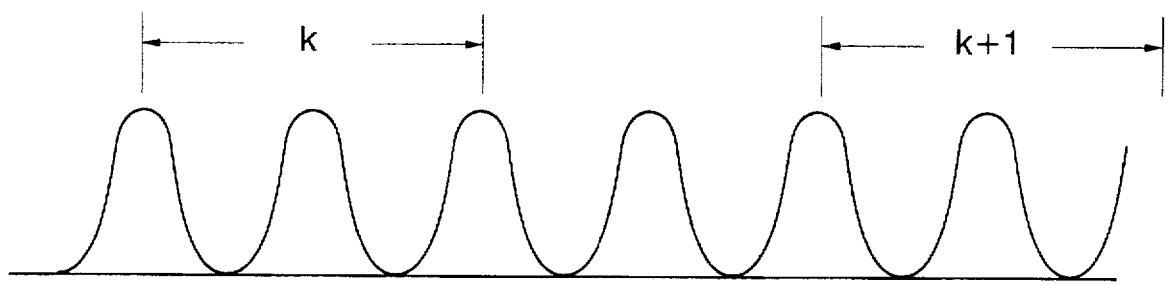

A number of methods may be used to perform adaptive parameter estimation including neural networks, Kalman filters, and ab trackers. Preferably, in the signal processor of the present invention, the adaptive tuning is accomplished using an αβ tracker, e.g., *Multiple-Target Tracking with Radar Applications*, S. S. Blackman, Artech House, Inc. (1986). The αβ tracker is preferred because it is computationally efficient and provides sufficiently accurate tracking. As used herein, the term "αβ tracker" refers to a method for updating the value of a variable in a data window based on (i) an initial value of a dependent variable; (ii) a present value of a dependent variable; and (iii) a present value of the first derivative of the dependent variable with respect to a relevant independent variable, e.g., time or position. As used herein, the term "data window" refers to a portion of the signal to which one cycle of the ab tracker is applied. See FIGS. 5A–C. The size of the data window is chosen such that the value of a within the window is essentially constant. Preferably the value of σ varies less than 10% across the window. More preferably, the value of σ varies less than 5% across the window. In a preferred embodiment, the size of the data window is constant throughout an analysis.

Figure 4:
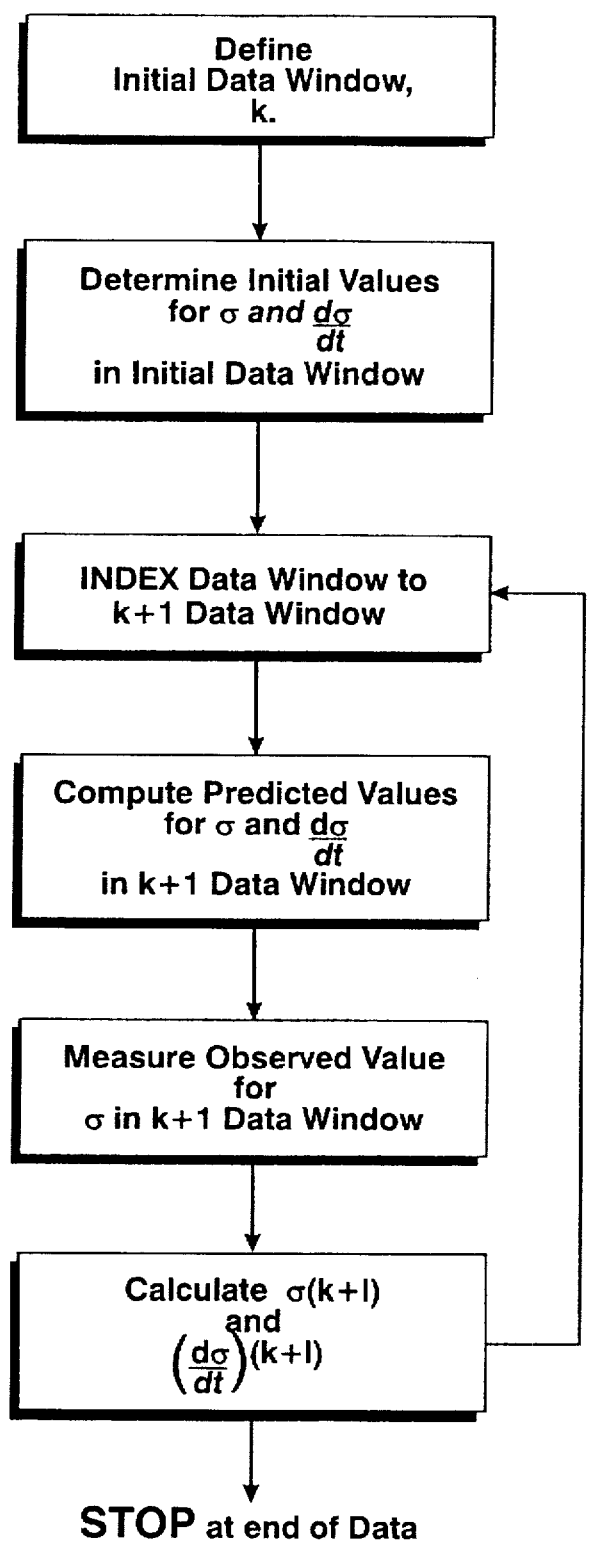
FIG. 4 is a flow chart of steps generally describing a preferred αβ-tracker utilized in the signal processor of the present invention.

The αβ tracker as applied to the present invention operates as follows. See FIG. 4. An initial value for σi(k) and dσi(k)/dt is obtained, where k is a data window index, the subscript i indicates an initial value, and t is time, the independent variable. σi(k) and dσi(k)/dt can be obtained in any manner resulting in a close approximation to the actual values of σi(k) and dσi(k)/dt. In one preferred method for obtaining initial values of σi(k) and dσi(k)/dt, estimates are based on previous experience with like systems.

In a second preferred method for obtaining initial values for σi(k) and dσi(k)/dt, values are measured directly from a data window in which such values can be accurately measured. For example, in the case of DNA sequencing, the early bases, i.e., between 20 and 100 nucleotides, are typically completely resolved. Thus, values of s can be easily measured using any peak-identification method, e.g., the 0-crossing method. (The 0-crossing method will be described hereinafter.) Given a measured value for σ, initial values of σi(k) and dσi(k)/dt may be readily calculated.

Once initial values for σi(k) and dσi(k)/dt have been established, the data window is indexed from the initial k window to the k+1 window. There are a number of different possible indexing alternatives. The k+1 window can be (i) immediately adjacent to the k window, FIG. 5A; (ii) partially overlap the k window, FIG. 5B; or (iii) be distant from the k window with uninterrogated data located between the k and k+1 windows, FIG. 5C. The choice of indexing method depends on several factors including (i) the magnitude of dσ/dt, (ii) the required accuracy, and (iii) the required computational speed.

If high accuracy is required, and slow computational speed can be tolerated, a high degree of overlap between the data windows is desirable, e.g., overlap of over 50%. As the requirement for accuracy is relaxed, computational speed may be increased by reducing the degree of overlap or by entirely eliminating any overlap. If the k+1 window is distant from the k window, an interpolation method is used to determine values for σi(k) and dσi(k)/dt in the uninterrogated inter-window regions.

Next, a predicted value for σ in the k+1 window, σp(k+1), is calculated. σp(k+1) is calculated for the k+1 window using the relation, $$\sigma_p(k+1) = \sigma_i(k) + T\left(\frac{d\sigma_i(k)}{dt(k)}\right)$$

where T is the distance between the center of data window k and the center of data window k+1.

Once a predicted value for s in the k+1 data window is obtained, an observed value for σ in the k+1 window, σo(k+1), is measured. Any number of well known methods may be used to measure σo(k+1). One preferred method is the "0-crossing" method wherein the value of σo(k+1) is taken to be proportional to the distance between two points at which $d^2\sigma/dt^2 = 0$.

Next, given values for σp(k+1) and σo(k+1), the αβ tracker equations are used to calculate values of σ(k+1) and dσ/dt(k+1), where, $$\sigma(k+1) = \sigma_p(k+1) + \alpha[\sigma_0(k+1) - \sigma_p(k+1)]$$

and, $$\frac{d\sigma}{dt}(k+1) = \frac{d\sigma}{dt}(k) + \frac{\beta}{T}[\sigma_0(k+1) - \sigma_p(k+1)]$$

where a and b are constants having values between 0 and 1.

The values of α and β determine the relative weight assigned to σo(k+1) and σp(k+1). If α=0, σ(k+1) is determined solely based on the predicted value of σ, σp(k+1), while if α=1, σ(k+1) is determined solely based on the observed value of σ(k+1), σo(k+1). The value chosen for a depends on the (i) rate of change of σ, i.e., magnitude of dσ/dt, and (ii) the accuracy of the method used to measure σo(k+1). When the rate of change of σ is high, and the accuracy of σo(k+1) is high, the observed value of σ is weighted more heavily then the predicted value, thus a is chosen to be large, e.g., 0.8. Alternatively, when the rate of change of σ is low, and the accuracy of σo(k+1) is low, the predicted value of σ is weighted more heavily then the observed value, thus α is chosen to be small, e.g., 0.2. In the worst case, when the rate of change of σ is high, and the accuracy of σo(k+1) is low, one wants to weight the predicted value of σ and the observed value of σ equally, thus a is chosen to be approximately 0.5. Preferred values of α range between 0.2 to 0.8. More preferably, α is between 0.4 and 0.6. The optimum value for β is determined from the value of a according to the relation, $$\beta = \frac{\alpha^2}{(2-\alpha)}.$$

The above steps are repeated until a PSF has been obtained for each of the data windows making up the signal.

In a third important aspect of the present invention, a plurality of possible values for the PSF are selected, and the largest value of the PSF which provides a non-negative result signal A(t) in a particular data window is used in the deconvolution method.

Fourier Transform of the Signal and the Point Spread Function:

Prior to deconvolving the signal and the PSF, the FT of the signal and the PSF is taken, thus transforming the signal and the PSF from the time or position domain to the frequency domain. Operating in the frequency domain makes the deconvolution process more computationally efficient because the deconvolution process becomes a multiplicative process in the frequency domain rather than a process requiring the solution of integral equations in the time or position domain. Preferably the FT is taken using a fast Fourier transform (FFT) technique, e.g., the Cooley-Tukey method. Before the FFT is applied to the signal, the signal in the window is "zero-padded" at either the beginning or the end of the window in order to eliminate aliasing effects due to overlap of neighboring sample windows.

Application of a Noise Filter and Deconvolution

In order to reduce the effect of system noise on the deconvolved result signal A(t), prior to deconvolving the transformed signal and PSF a Weiner filter is applied to the signal. As used herein, the term "system noise" refers to small random fluctuations in the signal resulting from fluctuations in components of the measurement device such as a radiation source, electronic circuitry, radiation detector, or any other like device-related source, or, from fluctuations in external environmental factors such as mechanical vibration, pick-up from 60-Hz electrical lines, temperature variations, or any other like environmental source.

System noise, n, is characterized by a frequency of greater than 2/Np, where Np is the approximate number of data points making up a single sample zone or peak. The value of n which is used in the Wiener filter is preferably a constant for a given data window. Preferably, n is empirically estimated from prior knowledge of the application.

One preferred method to determine a value for n is as follows. The FT of the random fluctuations in the signal is collected in a given data window, and the frequency at which the FT of the fluctuations does not appreciably change as a function of frequency is determined and the value of the FT of the fluctuations at that frequency is taken as the value of n.

The preferred filter used to reduce the effects of the system noise on the deconvolved result is a Weiner filter, e.g., *Fundamentals of Digital Image Processing*, A. K. Jain, pages 7 and 276, Prentice Hall, New Jersey (1989). A Weiner filter is defined by the function $$A(f) = \frac{(D(f)P^*(f))}{P^*(f)P(f) + n}$$

where A(f) is the Fourier transform of the result signal, D(f) is the Fourier transform of the signal, P(f) is the Fourier transform of the point-spread-function, P*(f) is the complex conjugate of P(f), and n is the system noise.

Computer

The steps of above-describe signal processing method are performed by a computer. Such computer can take the form of a generic microprocessor driven by appropriate software, a dedicated microprocessor using embedded firmware, or a customized digital signal processing circuit (DSP) which is dedicated to the specific data acquisition, analog-to-digital conversion, Fourier transformation, or filtering operation required by the signal processing method.

In one preferred embodiment, the computer comprises (i) a memory for storing a digitized representation of the signal, and (ii) a processor for carrying out the various steps of the signal processing method.

In such a case, the above method steps are embodied in a program storage device readable by a machine, such program storage device including a computer readable medium. Computer readable media include magnetic diskettes, magnetic tapes, optical disks, Read Only Memory, Direct Access Storage Devices, and any other like medium.

EXAMPLES

The invention will be further clarified by a consideration of the following examples, which are intended to be purely exemplary of the invention.

Example 1

Deconvolution of DNA Sequencing Data using the Method of the Invention

This example describes the results of an experiment applying the deconvolution method of the present invention to DNA sequencing data collected on a automated DNA sequencer; the Model 373 DNA Sequencer supplied by the Applied Biosystems Division of The Perkin-Elmer Corporation, Foster City, Calif. All of the data shown below was generated from the file named "Sample 21.1copy". The "Annotation View" from the Sequencing Analysis software for this file is shown immediately below.

| Data Collection | |
| --- | --- |
| File: | Sample 21.1 copy |
| Sample: | Sample 21.1 copy |
| Comment: | PGEM, A8, C9, G9, T10 |
| Lane Number: | 21 |
| Channel Number: | 108 |
| Number of Scans: | 10736 |
| Length: | 1240 |
| Run started at: | 1/6/1995, 15:05 |
| Run stopped at: | 2/6/1995, 09:03 |
| Gel: | Gel |
| Dyeset/Primer: | DP 4% Ac {−21M13} |
| Comb: | 36-well sharks-tooth |
| Instrument Name: | Machine 1115 |
| Collect Vers.: | N/A |
| Data Analysis | |
| Base Call Start: | 1033 |
| Base Call End: | 10736 |
| Primer Peak Loc.: | 1033 |
| Signal: | C (156), A (125), G (117), T (105) |
| Matrix Name: | Machine 1115 |
| Channels Ave.: | 3 |
| Analysis Vers.: | Version 2.2.0d2 |
| Base Spacing: | 8.56 - Basecaller++PPC |

The sequencing template was a pGEM 3Zf(+) plasmid. The sample was prepared according to standard protocols described in the document ABI Prism Dye Primer Cycle Sequencing Core Kit with AmpliTaq DNA Polymerase FS (ABD part number 402114, rev A, July 1995), with the exception that the nucleotide balance was slightly altered. The altered nucleotide balance is shown in the table immediately below.

| Reaction | ddNTP | dNTP |
| --- | --- | --- |
| A | 1.25 µM ddA | 500 µM ea dATP, dCTP, dGTP*, dTTP |
| C | 1.25 µM ddC | 500 µM ea dATP, dCTP, dGTP*, dTTP |
| G | 0.75 µM ddG | 500 µM ea dATP, dCTP, dGTP*, dTTP |
| T | 2.50 µM ddT | 500 µM ea dATP, dCTP, dGTP*, dTTP |

(*denotes 7-deaza dGTP)

The gel was poured using the standard 4% acrylamide as described in the 373 Stretch Instrument Manual (ABI p/n 903204). The migration distance for the electrophoresis was 48 cm. The electrophoresis was performed using standard conditions.

The deconvolution was performed on 3 regions of the data; early (bases 47–73), middle (bases 424–445), and late (bases 760–786). In each region, a constant Gaussian point spread function (PSF) was assumed. The parameters used for the deconvolution in each region are shown in the table immediately below.

| Region | Sigma | Width | Noise |
| --- | --- | --- | --- |
| Early | 2.00 | 4.70 | 1.00 |
| Middle | 3.00 | 7.05 | 1.00 |
| Late | 6.00 | 14.10 | 1.50 |

Figure 6A:
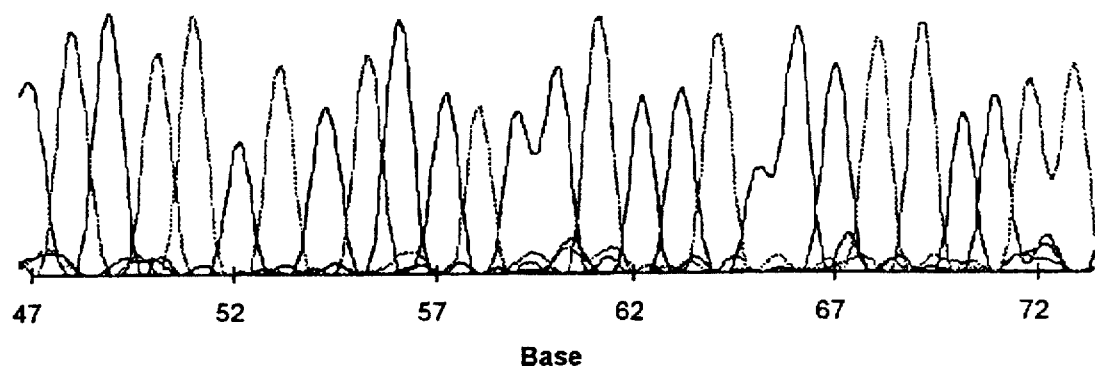
FIGS. 6A and 6B show DNA sequencing data obtained early in a run both before (top) and after (bottom) processing by the signal processor of the invention.
Figure 6B:
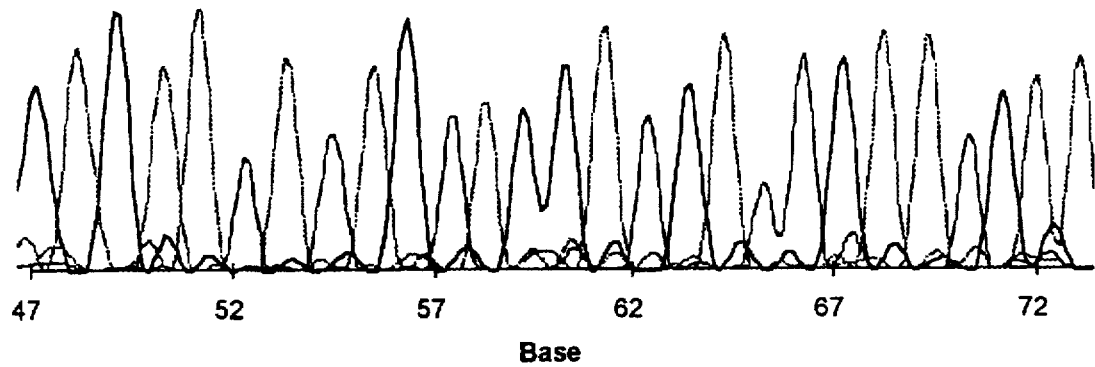
Figure 7A:
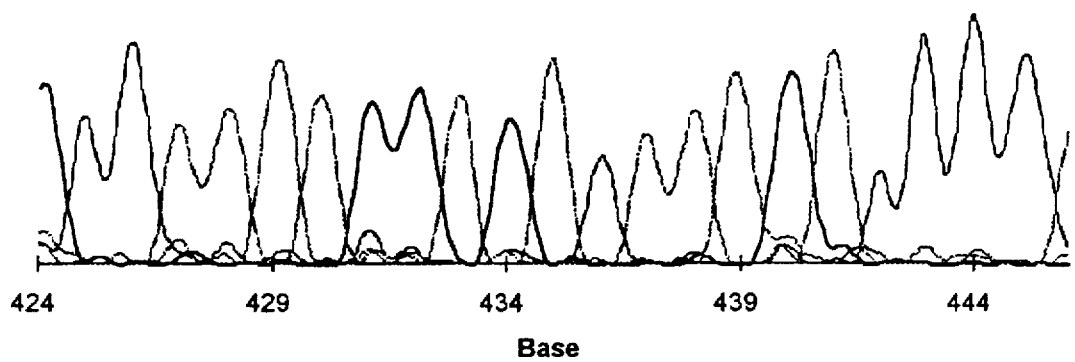
FIGS. 7A and 7B show DNA sequencing data obtained in the middle of a run both before (top) and after (bottom) processing by the signal processor of the invention.
Figure 7B:
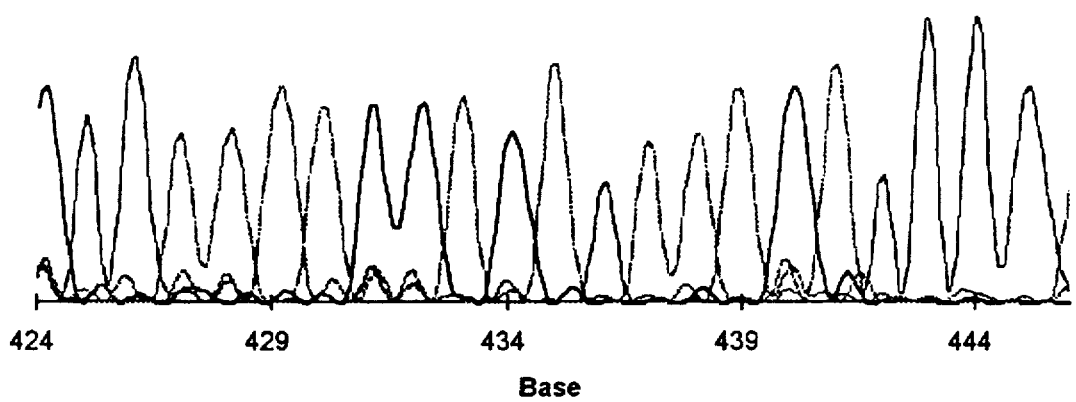
Figure 8A:
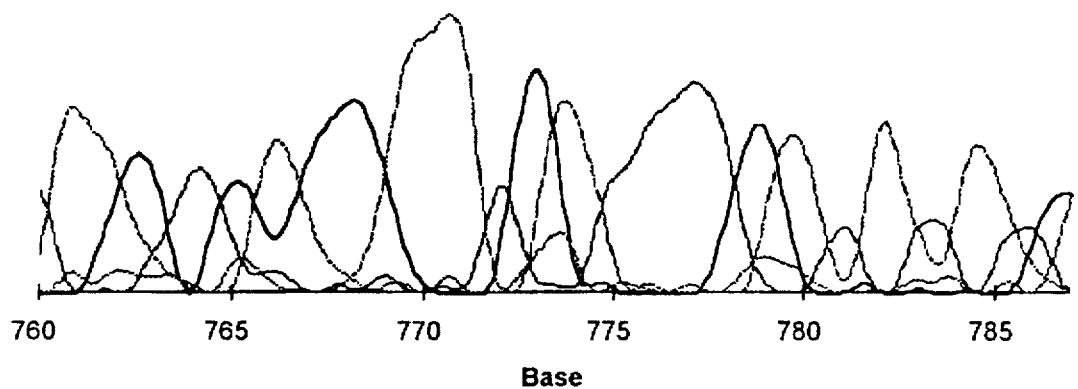
FIGS. 8A and 8B show DNA sequencing data obtained towards the end of a run both before (top) and after (bottom) processing by the signal processor of the invention.
Figure 8B:
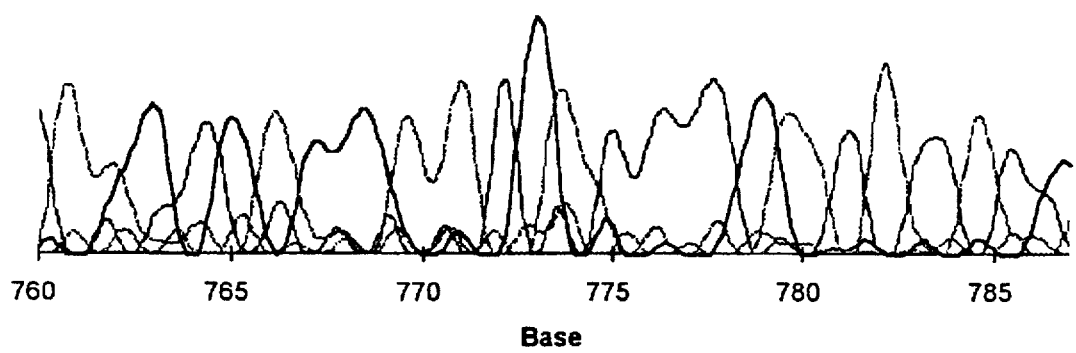

The results for each region are shown below. For each region, the data is shown before and after the deconvolution. Each window contains 300 data points. FIGS. 6A and 6B show data from the early region of the signal both before (top) and after (bottom) deconvolution; FIGS. 7A and 7B show data from the middle region of the signal both before (top) and after (bottom) deconvolution; and FIGS. 8A and 8B show data from the late region of the signal both before (top) and after (bottom) deconvolution.

We claim:

1. A signal processing method in a signal processor for identifying sample zones in a signal including multiple overlapping sample zones resulting from a separation process comprising the steps of:

receiving a signal generated by a detector which monitors the results of an analytical separation process, such signal representing a plurality of partially separated sample zones;

determining a point-spread-function of the signal;

converting the signal and the point-spread function from a time domain representation to a frequency domain representation using a Fourier transform;

determining a noise component of the signal;

calculating the value of a result signal A(f) using the formula $$A(f) = \frac{(D(f)P^*(f))}{P^*(f)P(f) + n},$$

where D(f) is the Fourier transform of the signal, P(f) is the Fourier transform of the point-spread-function, P*(f) is the complex conjugate of P(f), and n is the noise component of the signal; and converting the result signal A(f) from a frequency domain representation to a time domain representation by performing an inverse Fourier transform.

2. The method of claim 1 wherein the point-spread function is a Gaussian function having a standard deviation $\sigma$.

3. The method of claim 2 wherein $\sigma$ is determined using an $\alpha\beta$ tracker including a constant term $\alpha$ and a constant term $\beta$.

4. The method of claim 3 wherein the value of $\alpha$ is between 0.2 and 0.8.

5. The method of claim 3 wherein the value of a is between 0.4 and 0.6.

6. The method of claim 3 wherein $\beta = \alpha^2/(2-\alpha)$.

7. The method of claim 2 wherein $.\sigma = (a+bt^2)^{1/2}$.

8. A signal processing method in a signal processor for identifying sample zones in a signal including multiple overlapping sample zones resulting from a separation process comprising the steps of:

receiving a signal generated by a detector which monitors the results of an analytical separation process, such signal representing a distribution of partially separated sample zones;

providing a plurality of possible point-spread-functions of the signal;

converting the signal and each of the point-spread functions from a time domain representation to a frequency domain representation by taking the Fourier transform of each;

providing an estimate of a noise component of the signal;

calculating a result signal A(f) for each point-spread-function, where $$A(f) = \frac{(D(f)P^*(f))}{P^*(f)P(f) + n},$$

where D(f) is the Fourier transform of the signal, P(f) is the Fourier transform of the point-spread-function, P*(f) is the complex conjugate of P(f), and n is the noise component of the signal;

converting the result signal from the frequency domain to the time domain by taking the inverse Fourier transform of the result signal A(f) for each value of the point-spread function to give a result signal in the time domain A(t);

reporting the result signal A(t) in the time domain calculated using the largest value of the point-spread-function that provides a non-negative value of the result signal A(t).

9. A program storage device readable by a machine, tangibly embodying a program of instructions executable by a machine to perform method steps to identify sample zones resulting from a signal representing a plurality of partially separated sample zones, said method steps comprising:

receiving a signal generated by a detector which monitors the results of an analytical separation process, such signal representing a plurality of partially separated sample zones;

determining a point-spread-function of the signal;

converting the signal and the point-spread function from a time domain representation to a frequency domain representation by taking the Fourier transform of each;

determining a noise component of the signal;

calculating the value of a result signal A(f) using the formula $$A(f) = \frac{(D(f)P^*(f))}{P^*(f)P(f) + n},$$

where D(f) is the Fourier transform of the signal, P(f) is the Fourier transform of the point-spread-function, P*(f) is the complex conjugate of P(f), and n is the noise component of the signal; and converting the result signal A(f) from a frequency domain representation to a time domain representation by taking the inverse Fourier transform of the result signal.

* * * * *